US00PP25059P3

(12) United States Plant Patent
Greene

(10) Patent No.: US PP25,059 P3
(45) Date of Patent: Nov. 11, 2014

(54) ***ZOYSIA MATRELLA* PLANT NAMED 'BP7'**

(50) Latin Name: *Zoysia matrella*
Varietal Denomination: BP7

(76) Inventor: Homer C. Greene, Hobe Sound, FL (US)

( * ) Notice: Subject to any disclaimer, the term of this patent is extended or adjusted under 35 U.S.C. 154(b) by 321 days.

(21) Appl. No.: 13/507,754

(22) Filed: Jul. 26, 2012

(65) Prior Publication Data

US 2014/0033385 P1 Jan. 30, 2014

(51) Int. Cl.
*A01H 5/00* (2006.01)

(52) U.S. Cl.
USPC ..... Plt./390

(58) Field of Classification Search
USPC ..... Plt./390
See application file for complete search history.

*Primary Examiner* — Kent L Bell
(74) *Attorney, Agent, or Firm* — Sam McCoy

(57) ABSTRACT

A new and distinct cultivar of *Zoysia matrella* plant named 'BP7', characterized by the combination of a prostrate growth habit, deep green foliage color, fine foliage texture and improved lateral growth vigor; characteristics which translate to a turf grass with highly aesthetic color and texture that is fast to establish, exhibits improved environmental tolerances, and can be maintained at a low mowing height.

3 Drawing Sheets

Latin name of genus and species of plant claimed: The Latin name of the genus and species of the novel variety disclosed herein is *Zoysia matrella.*

Variety denomination: The novel variety of *Zoysia matrella* disclosed herein has been given the variety denomination 'BP7'.

REFERENCES CITED

U.S. Patent Documents

U.S. Plant Pat. No. 6,529, January 1989, Pursley

BACKGROUND OF THE INVENTION

The present invention relates to a new and distinct perennial variety of *Zoysia matrella,* which has been given the variety denomination of 'BP7'. Its market class is that of a turf grass. 'BP7' is intended for use as a lawn grass in gardening, landscaping, sports fields and amenity horticulture.

Parentage: The new *Zoysia matrella* cultivar is the result of a selection process originating as a spontaneous naturally occuring whole plate mutation that was discovered in a controlled, non-irrigated and shaded planting of *Zoysia matrella* (unpatented and unnamed) in Martin County, Fla., USA. The spontaneous mutation exhibited deep green foliage color, fine foliage texture, a prostrate growth habit and improved shade tolerance. Stolons of said spontaneous mutation were collected in August of 2010 for further evaluation and the confirmation of the distinctive characteristics observed in the field. Said stolons were planted into multiple nursery pots, using typical nursery production procedure at the Inventor's commercial turf grass farm in Martin County, Fla. The resultant nursery pots were observed from August of 2010 until April of 2011 at which point one nursery pot was selected as an exemplary specimen to the originally observed characteristics. Additionally, the Inventor observed that said specimen also exhibited improved drought tolerance, improved plant growth vigor and low seed head production. The new cultivar was given the designation of 'BP7'.

Asexual Reproduction: 'BP7' was first asexually propagated by cutting and division of stolons and rhizomes in April of 2011 in Martin Country, Fla. 'BP7' has since been further asexually propagated by means of cutting and division of stolons and rhizomes. The distinctive characteristics of the variety have remained stable and true to type through successive cycles of asexual propagation. Typical time to develop roots is similar to that of other *Zoysia* grasses; approximately 2 to 4 weeks and an average crop time to produce an initial mature and marketable stand of turf grass sod is approximately 8 to 12 months. Precise timing varies depending on fertilizer and water inputs as well as geographical location.

SUMMARY OF THE INVENTION

A new and distinct cultivar of *Zoysia matrella* plant named 'BP7', characterized by the combination of a prostrate growth habit, deep green foliage color, fine foliage texture and improved lateral growth vigor; characteristics which are of commercial value. The deep green foliage of 'BP7' is not only aesthetically appealing but the high concentration of chlorophyll which gives the foliage said deep green color also translates to greater efficiency of photosynthesis in lower light levels; i.e. improved shade tolerance. The prostrate growth habit and heavy branching at the nodes translates to a short and dense turf, capable of being maintained at a height of 1/16 in. (one sixteenth of an inch). The same said characteristics also means that 'BP7' is fast to establish, quick to recover from injury and also tolerant of heavy foot and machinery traffic; i.e. improved wear tolerance.

BRIEF DESCRIPTION OF THE PHOTOGRAPHS

DETAILED BOTANICAL DESCRIPTION

Figure 1:
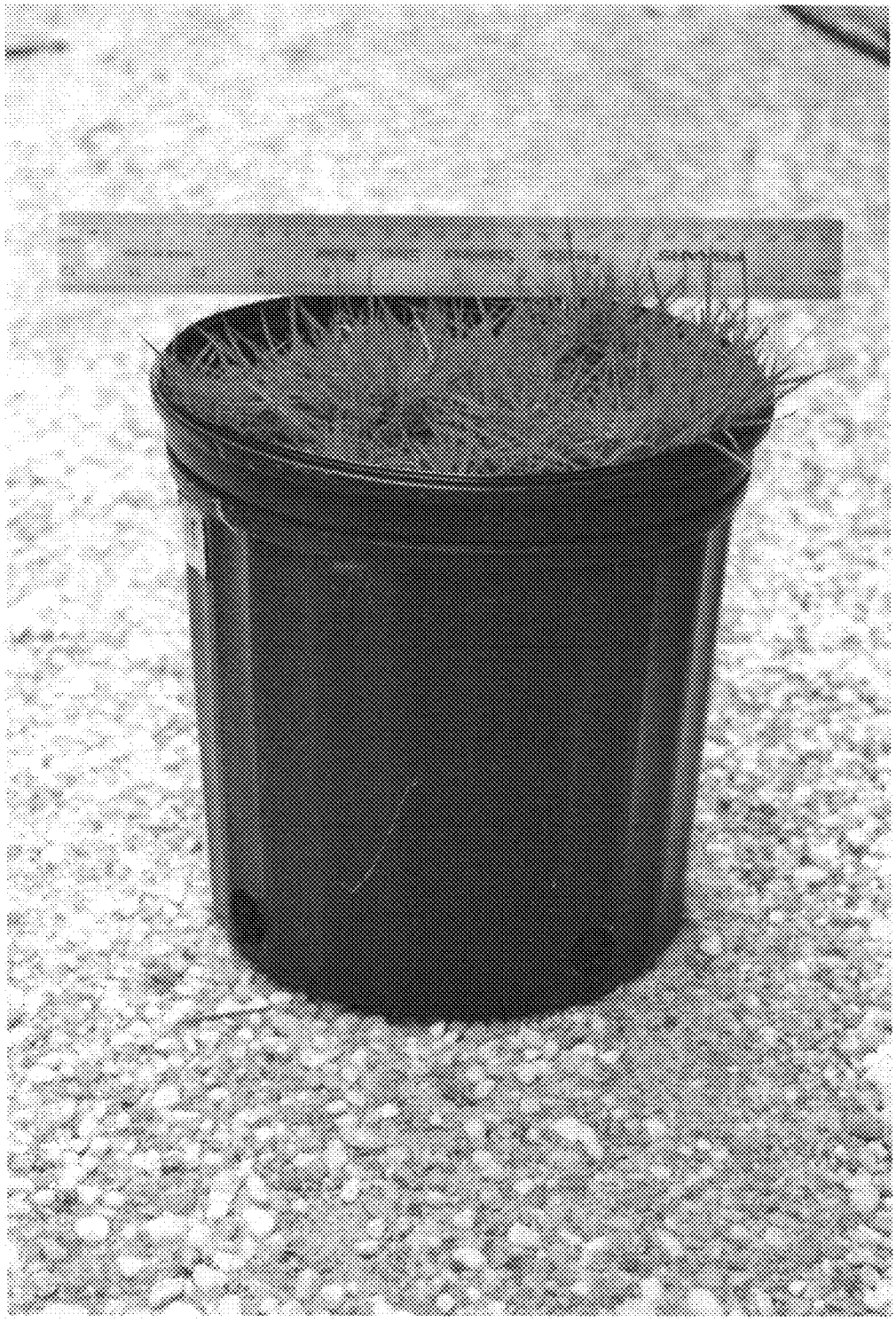
FIG. 1 illustrates, as nearly true as it is reasonably possible to make the same in color illustrations of this type, typical foliage and growth characteristics of the new cultivar. Colors in the photographs differ slightly from the color values cited in the detailed description, which accurately describes the colors of 'BP7'.
Figure 2:
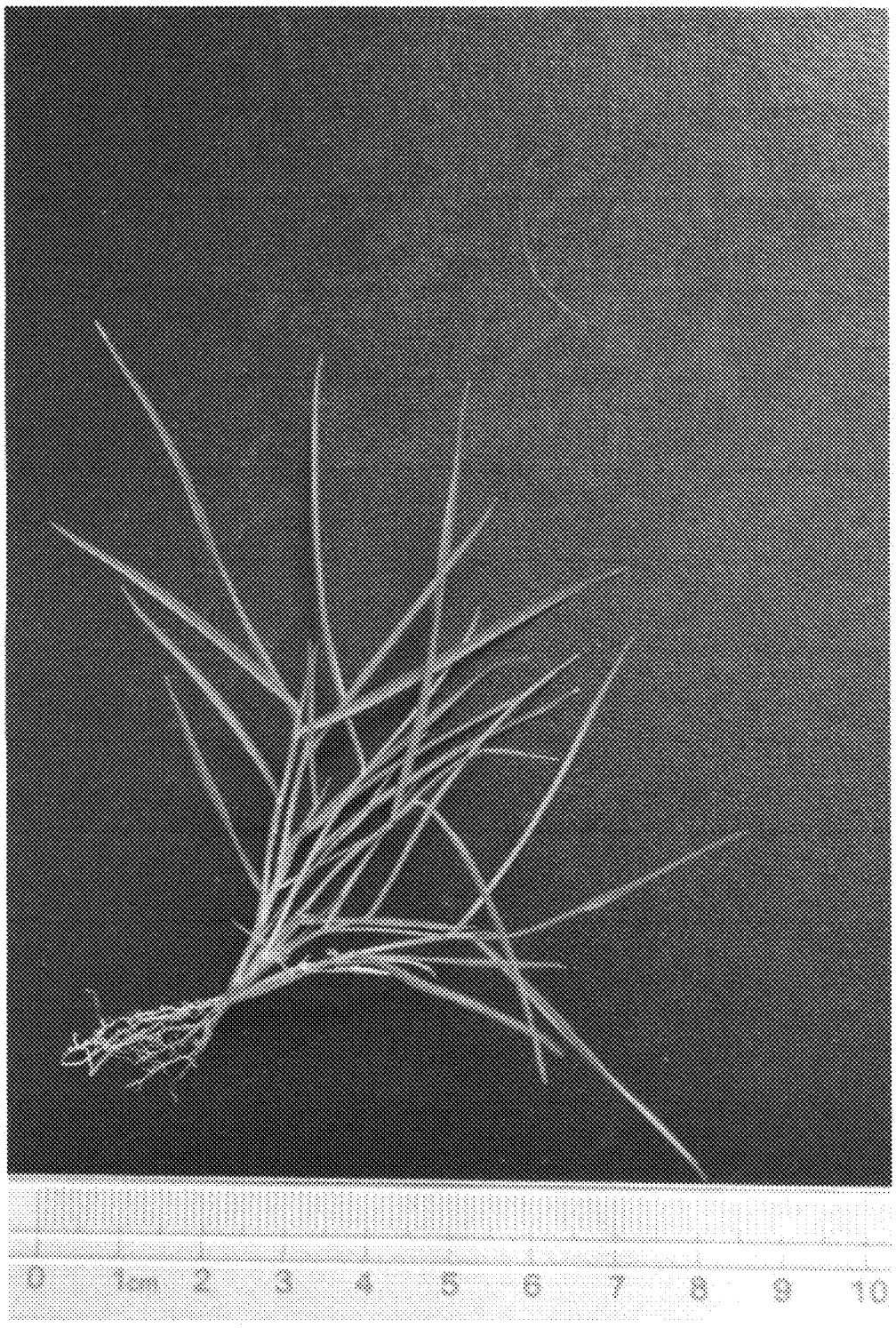
FIG. 2 illustrates the short culm length of 'BP7'.
Figure 3:
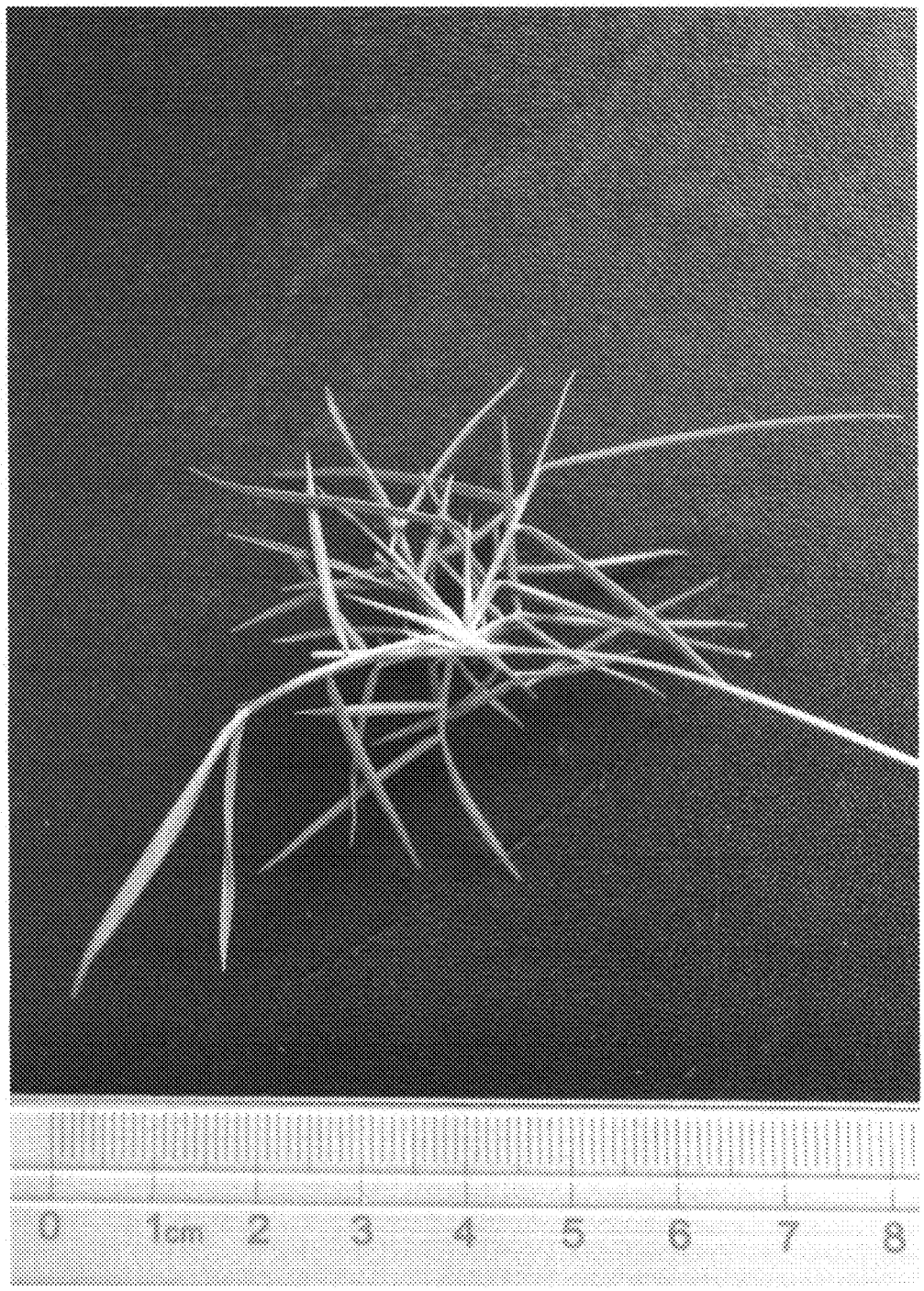
FIG. 3 illustrates the heavy branching at stolon nodes of 'BP7'.

The following is a detailed botanical description of a new and distinct variety of a *Zoysia matrella* turf grass plant known as 'BP7'. Plant observations were made on plants grown in Mt. Pleasant, S.C., USA. Unless indicated otherwise, the descriptions disclosed herein are based upon observations made in July 2011 of mature 'BP7' plants grown in 3 gallon nursery pots filled with soilless potting media, maintained with granular slow release fertilizer in an outdoor growing area and regularly watered with overhead irrigation. No pest and disease measures were taken. Daytime temperatures ranged from approximately 80° F. to 105° F. and night temperatures ranged from approximately 55° F. to 75° F. Plants were trimmed once, at two weeks after initial planting, and then grown for an additional 6 weeks before assessment.

Those skilled in the art will appreciate that certain characteristics will vary with older or, conversely, younger plants. 'BP7' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Color Chart, of The Royal Horticultural Society, London, 1986 edition.

Technical Description of the Variety.

Plant description:

- *Growth habit.*—Perennial plant with a prostrate growth habit forming a tight mat of stolons which root adventitiously on the ground surface and branch heavily at the stolon nodes. Culms are prostrate, becoming decumbent when flowering. Root system is typical for that of *Zoysia* grass species; a network or rhizomes and fibrous feeder roots.
- *Height.*—Measured from soil level, the canopy of 'BP7' exhibits a general approximate height of 4 cm with the tallest blades reaching 6 cm above soil level.
- *Growth rate.*—Moderate to vigorous.
- *Stolon length.*—Longest observed stolon is 16 cm.
- *Stolon width.*—Approximately 1 mm.
- *Stolon color* (*adaxial*).—Juvenile: Yellow-Green 146B; mature: Grayed Orange 176A.
- *Stolon color* (*abaxial*).—Juvenile: Yellow-Green 146B; mature: Yellow-Green 144C.
- *Stolon internode length.*—20 to 24 mm on mature stolons.

Foliage:

- *Attachment.*—Cauline.
- *Culm attitude.*—Prostrate to semi-decumbent when flowering.
- *Culm length.*—Ranging from 4 to 7 cm from stolon node to apex.
- *Culm internode length.*—Ranging from 2 to 10 mm.
- *Length of blade.*—Mature blades are an average of 60 mm.
- *Width of blade.*—1.5 mm on average.
- *Shape of blade.*—Linear.
- *Leaf shape; apex.*—Acute.
- *Leaf aspect.*—Concave.
- *Margin.*—Entire.
- *Texture of top surface.*—Glabrous.
- *Texture of bottom surface.*—Glabrous.
- *Leaf color* (*adaxial surface*).—Juvenile: 138A; mature: 139A.
- *Leaf color* (*abaxial surface*).—Juvenile: 138B; mature: 138B.
- *Venation: Type.*—Parallel.
- *Venation color.*—Indistinguishable.
- *Leaf sheath.*—Glabrous, ranging from 6 to 8 mm long. Color approximates to Green 138B.
- *Collar.*—Minute, less than 1 mm, and constricted. Color approximates to Yellow-Green 145C.
- *Ligule.*—Indistinguishable.

Flower:

- *Natural flowering season.*—Spring to fall; in Northern hemisphere, April to November.
- *Inflorescence type and habit.*—Spikelet.
- *Total inflorescence size.*—18 mm long by 1.5 mm wide.
- *Quantity of inflorescences.*—Less than the species; fewer than 10 per square foot.
- *Quantity of florets per spike.*—14 to 16 florets.
- *Color of florets.*—The immature lemmas are Yellow-Green (RHS 147B) and mature to a Grayed-Purple corresponding to 187A.
- *Dimensions of florets.*—Approximately 2.5 mm long and less than 1 mm wide.
- *Glumes:*—Absent.
- *Awns.*—Absent.
- *Rachilla.*—Curved; approximately 2.5 mm in length; width is minute; color is closest to Green 138B.

Reproductive organs:

- *Stamens.*—Not observed.
- *Style.*—Not observed in most grass, including 'BP7'.
- *Stigma.*—Featherlike; length is approximately 1 mm; wide is minute; color is Yellow-Green 154D.
- *Ovary.*—Not observed.

Seeds and fruits: Not observed.

Environmental tolerances:

- *Disease/pest resistance.*—Neither tolerance nor resistance to normal diseases and pests of *Zoysia matrella* has been observed.
- *Temperature tolerance.*—*Zoysia matrella* is known to tolerate temperatures from approximately 15 degrees F. to at least 115 degrees F.
- *Drought tolerance.*—Like other *Zoysia* species, 'BP7' exhibits good drought tolerance relative to other Genus of warm season grasses such as *Stenotaphrum* sp. Furthermore, 'BP7' has been observed to have improved drought tolerance by comparison with the closest comparator known to the breeder, *Zoysia* 'P-1' (U.S. Plant Pat. No. 6,529).
- *Soil tolerances.*—Tolerant of most soil types; from sandy loam to loamy clay.

Comparison of 'BP7' with Other Varieties of *Zoysia matrella*

The closest known variety to 'BP7' is *Zoysia matrella* 'P-1'. Both varieties are noted for dark green color, low growth habit, improved vigor and improved tolerances to certain environmental factors compared to the species. However, certain differences in the above noted characteristics distinguish 'BP7' as a novel and useful turf grass.

Both 'BP7' and 'P-1' are noted for deep green foliage color. However, 'BP7' is a deeper shade of green corresponding to RHS Green 139A whereas the foliage of 'P-1' corresponds to approximately RHS Green 137A or Green 137B (Yellowish Green No. 137 on the ISCC-NBS Centroid Color Chart).

Both 'BP7' and 'P-1' are noted for possessing a fine foliage texture. However, by using the length-to-width ratio of the lamina as a metric, the finer texture of 'BP7' can be quantified. The length to width ratio of 'BP7' is 40.0 (with an average length of 60.0 mm and average width of 1.5 mm) whereas the calculated ratio for 'P-1' is 33.3 (average length of 50.0 mm and width of 1.5 mm). Furthermore, when observing a cross section of the lamina of 'BP7' the aspect is concave whereas 'P-1' is flat. This concave aspect adds to the fine textured appearance of 'BP7'.

Both 'BP7' and 'P-1' are noted for a low growth habit. However, the shorter culm length and prostrate culm attitude of 'BP7' translates to a lower overall turf height capable of a mowing height as low as 1/16 in. (one sixteenth of an inch). 'BP7' has a mature culm length that ranges from 4 to 7 cm whereas the culm length of 'P-1' is 9 to 11 cm long. The culm attitude of 'BP7' is prostrate to semi-decumbent whereas the culm attitude of 'P-1' is decumbent.

Both 'BP7' and 'P-1' are noted for exhibiting vigorous growth. One metric used for quantifying lateral growth vigor is the ultimate length of the farthest reaching, mature stolons. The internode length of said stolons on 'BP7' is 20 to 24 mm whereas the internode length of said stolons on 'P-1' is 14 to 18 mm.

That which is claimed is:

1. A new and distinct variety of *Zoysia matrella* plant named 'BP7', substantially as described and illustrated herein.

* * * * *